United States Patent
Borden et al.

[11] Patent Number: 5,804,826
[45] Date of Patent: Sep. 8, 1998

[54] CARBON DIOXIDE LIQUID AND GAS SENSOR APPARATUS FOR USE WITH JET SPRAY CLEANING SYSTEMS

[75] Inventors: Michael R. Borden; Thomas J. Kosic, both of Redondo Beach, Calif.

[73] Assignee: Eco-Snow Systems, Inc., Livermore, Calif.

[21] Appl. No.: 850,873

[22] Filed: May 2, 1997

[51] Int. Cl.⁶ .................................................. G01N 21/41
[52] U.S. Cl. .......................................... 250/343; 356/128
[58] Field of Search ............................... 250/343, 341.1, 250/356.1; 356/128

[56] References Cited

U.S. PATENT DOCUMENTS 5,452,076  9/1995  Schopper et al. ...................... 356/128

*Primary Examiner*—Edward J. Glick
*Assistant Examiner*—Darren M. Jiron
*Attorney, Agent, or Firm*—R. Craig Armstrong

[57] ABSTRACT

Detection apparatus for use with a carbon dioxide jet spray cleaning system that determines whether liquid carbon dioxide is flowing between a storage tank and a jet spray nozzle. The detection apparatus determines whether carbon dioxide snow is generated by the jet spray nozzle, which is produced by expansion of liquid carbon dioxide through the jet spray nozzle. The apparatus comprises a transfer tube coupled between the storage tank and the jet spray nozzle that has transparent input and output windows and which permits liquid carbon dioxide to flow from the storage tank to the jet spray nozzle. A light source produces light that is focused on a pinhole in an aperture stop. A collimating lens images collimated light on the input window of the transfer tube, and a light detector detects light that is refracted by liquid carbon dioxide in the transfer tube that exits through the output window and is incident thereon, and generates an output signal indicating light detection. The output signal indicates that liquid carbon dioxide is flowing between the storage tank and the jet spray nozzle, and thus that snow is generated.

9 Claims, 1 Drawing Sheet

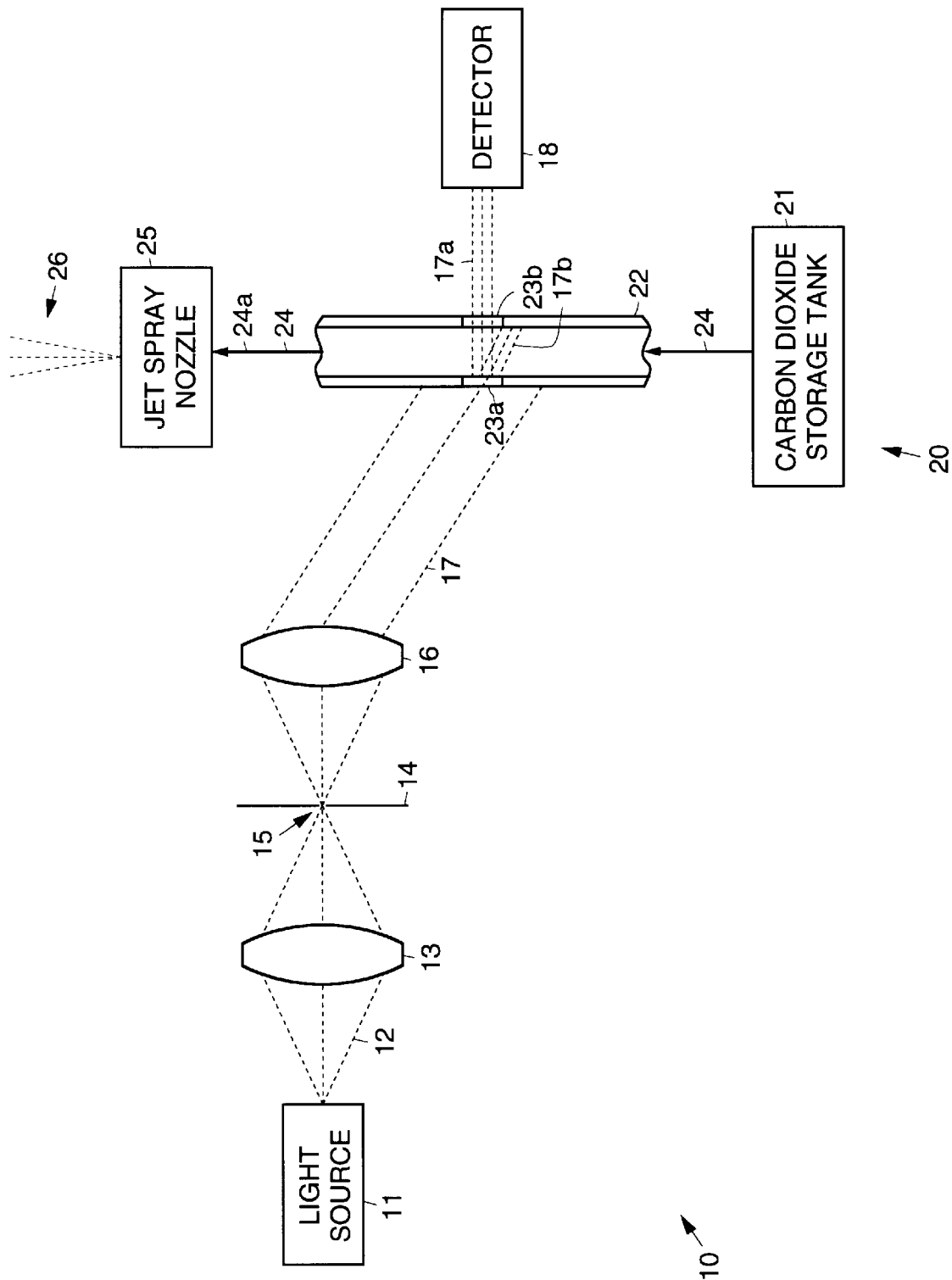

CARBON DIOXIDE LIQUID AND GAS SENSOR APPARATUS FOR USE WITH JET SPRAY CLEANING SYSTEMS

BACKGROUND

The present invention relates generally to cleaning systems, and more particularly, to a sensor system for use with carbon dioxide jet spray cleaning systems.

The assignee of the present invention manufactures carbon dioxide jet spray cleaning systems that generate a spray of carbon dioxide snow produced by expanding liquid carbon dioxide through a jet spray nozzle. The liquid carbon dioxide is stored in a storage tank under pressure and is transferred to the jet spray nozzle which produces a jet spray plume of carbon dioxide that is used to clean optical and semiconductor components, for example, during manufacture.

These optical and semiconductor component manufacturing systems are highly automated, and therefore the carbon dioxide jet spray cleaning systems must be integrated into the manufacturing process and must also be automated. When liquid phase carbon dioxide flows from the tank to the nozzle, the carbon dioxide snow necessary for cleaning is produced at a jet spray nozzle. Unfortunately, no snow is formed when the liquid carbon dioxide has expired or when the liquid drops below the level of an internal siphon tube and gaseous carbon dioxide flows from the storage tank.

It would therefore be advantageous to have apparatus for use with carbon dioxide jet spray cleaning systems that provides a means for making such cleaning systems automatic so that they may be integrated into manufacturing systems that manufacture semiconductor and optical components, and the like. Accordingly, it is an objective of the present invention to provide for such an apparatus.

SUMMARY OF THE INVENTION

To meet the above and other objectives, the present invention provides for the use of a light source that produces a beam of light that is passed through transparent windows disposed in a carbon dioxide transfer tube coupled between a carbon dioxide storage tank and a jet spray nozzle to determine whether liquid or gaseous carbon dioxide ($CO_2$) is flowing through the tube. Such apparatus is necessary in automated carbon dioxide jet spray cleaning systems to determine when liquid carbon dioxide is flowing from the storage tank. Carbon dioxide snow spray necessary for cleaning is produced at the jet spray nozzle when liquid carbon dioxide flows from the tank to the nozzle. No snow is formed when the liquid carbon dioxide is expired or when the liquid drops below a level of an internal siphon tube in the tank and gaseous carbon dioxide flows out of the tank.

In a preferred embodiment, the present invention uses a low cost, light emitting diode operating at a wavelength of 850 nanometers, for example. Light from the light emitting diode is coupled through a pinhole and is collimated. The collimated light passes through windows in the transfer tube at a relatively large angle, typically on the order of 30 degrees, for example. A detector intercepts the light after it exits the transfer tube, after it is refracted by the liquid carbon dioxide, because the refractive index of the liquid carbon dioxide is greater than 1 (the absorption of carbon dioxide is low ($k<0.0001$) at a wavelength of 850 nanometers). Since the refractive index of the gaseous carbon dioxide is much lower (greater than 30 percent lower) than that of the liquid carbon dioxide, light passing through the tube when gas is present in the tube is not refracted to the same degree as when the liquid is present in the tube, and therefore would not be imaged onto and detected by the detector. The signal produced by the detector provides an indication that there is insufficient liquid carbon dioxide in the storage tank to properly generate carbon dioxide snow used for cleaning. Therefore, the present invention provides for a sensor that determines when the carbon dioxide jet spray system can be operated automatically.

The present invention has a significant advantage over devices that look for the difference between that amount of carbon dioxide snow versus gas exiting the jet spray nozzle, since the present invention does not interfere with the end of the nozzle and obscure the hardware that is being cleaned. The ability to have an obscuration-free nozzle area also aids in locating the tip of the nozzle when programming cleaning recipes for intricate hardware.

BRIEF DESCRIPTION OF THE DRAWINGS

The various features and advantages of the present invention may be more readily understood with reference to the following detailed description taken in conjunction with the accompanying drawing FIGURE, which is a side view of detection apparatus in accordance with the principles of the present invention for use with a carbon dioxide jet spray cleaning system that determines whether liquid carbon dioxide is flowing between a storage tank and a jet spray nozzle and thus whether carbon dioxide snow is being generated by the jet spray nozzle.

DETAILED DESCRIPTION

Referring to the drawing FIGURE, it illustrates detection apparatus 10 in accordance with the principles of the present invention for use with a carbon dioxide jet spray cleaning system 20 that determines whether liquid carbon dioxide 24 is flowing between a storage tank 21 and a jet spray nozzle 25 and thus whether carbon dioxide snow 26 is generated by the jet spray nozzle 25. The carbon dioxide snow 26 is produced by expansion of liquid carbon dioxide 24 through the jet spray nozzle 25. When gaseous carbon dioxide 24a flows through the jet spray nozzle 25, the snow 26 is not produced.

The liquid carbon dioxide 24 is transferred out of the storage tank 21 by means of a siphon tube in the tank. When liquid carbon dioxide 24 is depleted, or when its level drops below the siphon tube, gaseous carbon dioxide flows out of the storage tank 21 and thus the carbon dioxide snow 26 is not produced. The carbon dioxide jet spray cleaning system 20 is provided with a transfer tube 22 that has transparent input and output windows 23a, 23b that are transparent to light 17 at a predetermined wavelength. The transfer tube 22 may be comprised of stainless steel, for example. The transparent input and output windows 23a, 23b may be comprised of sapphire, for example.

The detection apparatus 10 comprises a light source 11, such a light emitting diode 11 operating at a wavelength of 850 nanometers, for example. If required, a focusing lens 13 is disposed in front of the light source 11 which is used to focus light 12 produced by the light source 11 to a point. An aperture stop 14 having a pinhole 15 therein is disposed at the primary focal plane of the focusing lens 13. The focused light 12 is caused to pass through the pinhole 15. The light source 11 may be designed to have a built in focusing lens at its output which focuses the light 12 generated by the light source. In this case, the focusing lens 13 would not be necessary.

A collimating lens 16 is disposed on a distal side of the aperture stop 14 from the light source 11 and produces collimated light 17 that is imaged on the input window 23*a* of the transfer tube 22. The collimated light 17 is imaged on the input window 23*a* at a relatively large angle, typically on the order of 30 degrees, for example. When liquid carbon dioxide 24 is flowing through the transfer tube 22, the collimated light 17 entering the tube 22 through the input window 23*a* is refracted at an angle that causes it to exit through the output window 23*b*. The collimated light 17 exiting through the output window 23*b* is incident upon a light detector 18 that generates an output signal indicating this detection of light.

However, when gaseous carbon dioxide 24*a* is flowing through the transfer tube 22, the collimated light 17 entering the tube 22 through the input window 23*a* is refracted at less of an angle than when liquid carbon dioxide is present in the tube 22. As a result, the collimated light 17 does not exit through the output window 23*b* when gaseous carbon dioxide 24*a* is present in the tube 22 and is therefore not detected by the detector 18. Thus, the light detector 18 does not generates an output signal. The "on-off" state of the output signal generated by the detector 18 thus indicates the presence of liquid or gaseous carbon dioxide in the transfer tube 22.

More specifically, the refractive index of the liquid carbon dioxide 24 is greater than 1, and the absorption of carbon dioxide is low (k<0.0001) at a wavelength of 850 nanometers. The refractive index of the gaseous carbon dioxide 24*a* is much lower (more than 30 percent lower) than liquid carbon dioxide 24. Therefore, light 17 passing through the tube 22 when gaseous carbon dioxide 24*a* in present therein is not refracted to the same degree as when the liquid carbon dioxide 24 is present in the tube 22, and therefore is not imaged onto or detected by the detector 18. The signal produced by the detector 18 thus provides an indication that there is insufficient liquid carbon dioxide 24 in the storage tank 21 to generate the carbon dioxide snow spray 26 used for cleaning. The detection apparatus 10 thus provides a sensor that indicates when the carbon dioxide jet spray system 20 can be automatically operated.

The output signal generated by the detector 18 may be used to generate a warning signal to an operator of the carbon dioxide jet spray cleaning system 20 that the liquid carbon dioxide in the storage tank is substantially depleted and that operation of the system 20 should be terminated. Alternatively, the output signal generated by the detector 18 may be used to temporarily stop the cleaning operation of the system 20 while new storage tank 21 is coupled to the system 20, although this is not preferred in an automated manufacturing process. Preferably, in an automated manufacturing process, the output signal generated by the detector 18 is used to generate a warning signal to an operator that the liquid carbon dioxide in the storage tank is substantially depleted and to couple a new storage tank 21 to the system 20. The detection apparatus 10 may be readily adjusted to generate an output signal from the detector 18 that gives an operator time to couple a new storage tank 21 to the system 20 prior to the time that the carbon dioxide spray 26 is not present.

Thus, detection apparatus 10 for use with a carbon dioxide jet spray cleaning system 20 that determines whether liquid carbon dioxide 24 is flowing between a storage tank 21 and a jet spray nozzle 25 and thus whether carbon dioxide snow 26 is being generated by the jet spray nozzle 25 has been disclosed. It is to be understood that the described embodiment is merely illustrative of some of the many specific embodiments which represent applications of the principles of the present invention. Clearly, numerous and other arrangements can be readily devised by those skilled in the art without departing from the scope of the invention.

What is claimed is:

1. Apparatus for use with a carbon dioxide jet spray cleaning system having a storage tank for storing liquid carbon dioxide under pressure and a jet spray nozzle, for determining if carbon dioxide snow spray is generated by the jet spray nozzle, said apparatus comprising:

a transfer tube coupled between the storage tank and the jet spray nozzle that has transparent input and output windows that are transparent to light at a predetermined wavelength, and which permits the flow of liquid carbon dioxide from the storage tank to the jet spray nozzle;

a light source for producing light;

an aperture stop having a pinhole therein disposed such that light from the light source is caused to pass through the pinhole;

a collimating lens for generating collimated light and imaging the collimated light on the input window of the transfer tube; and a light detector disposed adjacent to the output window, for detecting light that is refracted by liquid carbon dioxide passing through the transfer tube and that exits through the output window and is incident thereon, and for generating an output signal indicating light detection.

2. The apparatus of claim 1 wherein the light source comprises a light emitting diode.

3. The apparatus of claim 2 wherein the light emitting diode produces light having a wavelength of 850 nanometers.

4. The apparatus of claim 1 further comprising a focusing lens for focusing light produced by the light source, and wherein the aperture stop is disposed at a primary focal plane of the focusing lens.

5. Apparatus for use with a carbon dioxide jet spray cleaning system having a storage tank and a jet spray nozzle, for determining if carbon dioxide snow spray is generated, said apparatus comprising:

a transfer tube coupled between the storage tank and the jet spray nozzle that has transparent input and output windows that are transparent to light at a predetermined wavelength;

a light source for producing light;

an aperture stop having a pinhole therein disposed such that light from the light source is caused to pass through the pinhole;

a collimating lens for generating collimated light and imaging the collimated light on the input window of the transfer tube; and a light detector disposed adjacent to the output window, for detecting light that exits through the output window and is incident thereon, and for generating an output signal indicating light detection;

and wherein, when liquid carbon dioxide is flowing through the transfer tube, the collimated light entering the tube through the input window is refracted at a predetermined angle that causes it to exit through the output window and impinge upon the light detector which generates the output signal indicating light detection, and wherein when gaseous carbon dioxide is flowing through the transfer tube, the collimated light entering the tube through the input window is refracted at an angle less than the predetermined angle so that the collimated light does not exit through the output window and is not detected by the detector, so that the light detector does not generate the output signal, and wherein the state of the output signal generated by the detector indicates the presence of liquid or gaseous carbon dioxide in the transfer tube.

6. The apparatus of claim 5 wherein the light source comprises a light emitting diode.

7. The apparatus of claim 6 wherein the light emitting diode produces light having a wavelength of 850 nanometers.

8. The apparatus of claim 5 further comprising a focusing lens for focusing light produced by the light source, and wherein the aperture stop is disposed at a primary focal plane of the focusing lens.

9. The apparatus of claim 5 wherein the predetermined angle is about 30 degrees.

* * * * *